US008486430B2

(12) United States Patent
Johnston et al.

(10) Patent No.: US 8,486,430 B2
(45) **Date of Patent: *Jul. 16, 2013**

(54) ADJUSTABLE DENSITY, PARTIALLY WATER-DISPERSIBLE CARRIER FOR ACTIVE AGENTS

(75) Inventors: Matthew G. Johnston, Centennial, CO (US); James R. Lynch, Toledo, OH (US); Timothy D. Birthisel, Perrysburg, OH (US)

(73) Assignee: The Andersons, Inc., Maumee, OH (US)

( * ) Notice: Subject to any disclaimer, the term of this patent is extended or adjusted under 35 U.S.C. 154(b) by 274 days.

This patent is subject to a terminal disclaimer.

(21) Appl. No.: 11/843,409

(22) Filed: Aug. 22, 2007

(65) Prior Publication Data

US 2008/0051290 A1 Feb. 28, 2008

Related U.S. Application Data

(60) Provisional application No. 60/823,264, filed on Aug. 23, 2006.

(51) Int. Cl.

| | |
|---|---|
| ***A01N 25/00*** | (2006.01) |
| ***A01N 25/08*** | (2006.01) |
| ***A01N 25/24*** | (2006.01) |
| ***A01N 47/10*** | (2006.01) |
| ***A01N 53/10*** | (2006.01) |

(52) U.S. Cl.
USPC ........... 424/405; 424/410; 504/367; 514/479; 514/531

(58) Field of Classification Search
USPC .................. 424/410, 405; 504/367; 514/479, 514/531
See application file for complete search history.

(56) References Cited

U.S. PATENT DOCUMENTS

| | | | | |
|---|---|---|---|---|
| 3,617,246 | A * | 11/1971 | Duyfjes et al. | 504/367 |
| 3,849,105 | A | 11/1974 | Woods | |
| 3,966,641 | A | 6/1976 | Csatar et al. | |
| 4,187,803 | A | 2/1980 | Valenta | |
| 4,579,579 | A | 4/1986 | Kerr | |
| 4,844,734 | A | 7/1989 | Iwasaki et al. | |
| 5,041,410 | A * | 8/1991 | Ivie | 502/401 |
| 5,242,690 | A * | 9/1993 | Moechnig | 424/405 |
| 5,837,275 | A | 11/1998 | Burrell et al. | |
| 5,843,203 | A | 12/1998 | Lindsay et al. | |
| 6,180,565 | B1 | 1/2001 | Detrick | |
| 6,613,138 | B2 * | 9/2003 | Welshimer et al. | 106/405 |
| 7,160,841 | B2 | 1/2007 | Fujita et al. | |
| 2005/0175577 | A1 * | 8/2005 | Jenkins et al. | 424/76.1 |
| 2006/0121075 | A1 | 6/2006 | Gilo et al. | |
| 2006/0252649 | A1 | 11/2006 | Pluta et al. | |
| 2007/0082821 | A1 | 4/2007 | Welshimer et al. | |
| 2007/0098752 | A1 | 5/2007 | Gilo et al. | |

FOREIGN PATENT DOCUMENTS

WO WO 2005/097071 A2 10/2005

OTHER PUBLICATIONS

Goss, G.R., Taylor, D.R., and Kallay, W.B., "Granular Pesticide Formulations," Pesticide Formulations and Application Systems: 15th Volume, ASTM STP 1268, Herbert M. Collins, Franklin R. Hall, and Michael Hopkinson, Eds., American Society for Testing and Materials, Philadelphia, 1994.*

* cited by examiner

*Primary Examiner* — Fereydoun G Sajjadi
*Assistant Examiner* — Courtney Brown
(74) *Attorney, Agent, or Firm* — Blue Filament Law PLLC; Avery N. Goldstein; Marc S. Balban

(57) ABSTRACT

A vegetation culture active agent delivery medium is provided that includes dense mineral granules, comparatively less dense cellulosic granules, and an active agent in simultaneous contact with the mineral granules and the cellulosic granules, the active agent present from $1\times10^{-5}$ to 10 total weight percent of the medium. A formulation of an active agent is applied to one type of granule as a mixture thereof. Through control of the relative amounts of mineral and cellulosic granules, a controlled medium density is readily adjusted between 35 and 60 pounds per cubic foot.

19 Claims, No Drawings

ADJUSTABLE DENSITY, PARTIALLY WATER-DISPERSIBLE CARRIER FOR ACTIVE AGENTS

CROSS-REFERENCE TO RELATED APPLICATIONS

This application claims priority benefit of U.S. Provisional Application Ser. No. 60/823,264, entitled "Adjustable Density, Partially Water-Dispersible Carrier for Active Agents", filed Aug. 23, 2006, which is incorporated herein in its entirety.

FIELD OF THE INVENTION

The present invention in general relates to pelletized particles for the delivery of an active agent and in particular to particles with variable density partial dispersibility in water as carriers.

BACKGROUND OF THE INVENTION

With a greater appreciation as to environmental damage associated with pesticide usage, there are ever-increasing limitations as to the classes of chemical compounds suitable as pesticides, as well as limitations when those pesticides can be spread on a crop. In many cases, in order to ameliorate environmental damage associated with pesticide application, pesticide use is mandated during seasons when the pest lifecycle is at the most vulnerable stage to limit dosing and collateral ecological toxicity. As integrated pest management has been endorsed by environmental regulatory agencies, industry associations and entomologists, more judicious pesticide usage should be expected in the future.

An ongoing problem in minimizing pesticide usage is the difficulty in delivery of a pesticide efficiently to a target plant within a large area of cultivated vegetation. A practical labor-saving approach to pesticide delivery to such as golf courses, parks, lawns, gardens and agricultural fields has been broadcast application of granular products containing a pesticide with equipment such as a rotary spreader. Using granular products having particle sizes in the range of about 1 millimeter to about 10 millimeters, an operator can cover a large area with minimal distance traversed by the spreader itself while at the same time applying the granular active agent with relative uniformity over the desired area. Unfortunately, such granular active agents often remain in solid or semisolid form for a considerable time following application. Since the pesticide is typically physically bound within the granule, the active agent efficacy is reduced or delayed, potentially resulting in a loss of product activity via volatilization or photodegradation with the consequence of lower efficacy and higher cost.

A further consequence of granular active agent distribution is that the granules are subject to removal by plant culture operations such as mowing or aerating, or environmental factors such as wind and rain, especially on sloping ground where the underlying soils have low percolation rates, where ground cover is sparse or areas of high foot traffic. The ability to adjust material density to respond to high wind dispersion areas and other such environmental factors has met with limited success as no single material has all the desired properties of formulation densities over a range with regard to cost, processability, transport stability, and dust formation.

A material that has a high density of active agent per unit mass of granular material tends to be spread with an excess of active agent used per unit area of ground, while low density material tends to be underutilized per unit area of ground. As most vegetation culture granular products are sold by total weight instead of active agent density per unit mass, the ability to adjust product density is important in packaging operations.

The inability to control uniformity in active agent application and therefore efficacy is altered due to excessive concentration of the product within certain treated areas while other areas suffer diminished active agent concentrations. Additionally, a long-persistent granule creates a greater likelihood that people and beneficial insects and other animals will come into physical contact with the granules, resulting in undue human health effects and environmental degradation. An alternative to long-persistent granule products is spray application of a liquid active agent. Unfortunately, spray treatments require considerable skill for application and result only in contact to exposed foliage with other surfaces receiving only indirect drainage from exposed foliage. Additionally, spray treatment tends to dissipate quickly. Due to spray atomization of liquid active agents, a considerable amount of active agent is lost through volatilization and wind drift thereby requiring greater quantities to reach pests dwelling on the underside of foliage. The net result is inefficient pesticide usage; non-target hazard effects to people, wildlife, and non-target property; as well as other deleterious effects of pesticides, such as leaching into the soil through rain contact causing environmental wastewater management issues.

Thus, there exists a need for a plant culture delivery medium for carrying of active substance amenable to the density modification.

SUMMARY OF THE INVENTION

A vegetation culture active agent delivery medium is provided that includes dense mineral granules, comparatively less dense cellulosic granules, and an active agent in simultaneous contact with the mineral granules and the cellulosic granules, the active agent present from $1\times10^{-5}$ to 10 total weight percent of the medium. A formulation of an active agent is applied to one type of granule as a mixture thereof. Through control of the relative amounts of mineral and cellulosic granules, a controlled medium density is readily adjusted between 35 and 60 pounds per cubic foot.

DETAILED DESCRIPTION OF THE PREFERRED EMBODIMENTS

The present invention has utility as a medium to deliver an active agent as a part of a vegetation culture. The use of an inventive blend achieves superior handling and efficiency of active ingredient usage as compared to the conventional art and affords the manufacturing advantage of tailoring media total density to properly fill packaging. Preferably, one blend component of the delivery media disintegrates on contact with water so as to inhibit unintended secondary spreading of inventive blend granules.

In order to overcome prior art difficulties, an inventive active agent delivery medium includes in combination between 10 and 90 total weight percent of a dense mineral granule, a comparatively less dense cellulosic granule present from 10 to 90 total weight percent of the medium, and an active agent in simultaneous contact with the mineral granules and the cellulosic granules, the active agent present from $1\times10^{-5}$ to 10 total weight percent of the medium. Through the combination of granules of two different densities in an inventive vegetation culture active agent delivery medium, a formulator is able to vary the ratio of different granule types to provide a specific density by varying the amount of mineral granules and the cellulosic granules. In this way, a specific density is achieved without resort to granule reformulation; rather, mixing of dense mineral granules with cellulosic granules in a predetermined weight ratio achieves this result with high efficiency. A medium density controlled between 35 and 60 pounds per cubic foot allows for medium spreading tailored to factors such as spreader distribution rate, wind conditions, and the grade of the soil area.

A mineral granule of an inventive combination is sized for broadcast distribution and inert towards a contacting active agent. A mineral granule contains at least 30 mineral granule weight percent of a mineral having a bulk density of at least 70 pounds per cubic foot to afford a mineral granule density of at least 70 pounds per cubic foot. A mineral fragment of a mineral granule operative herein illustratively includes powdered dolomite, limestone, gypsum, and pelletized lime. Typically, a mineral granule has a mean particle size of from 500 to 3000 microns and is formed from two or more mineral fragments aggregated together with a binder. Preferably, an aggregate granule is formed through the mixture of a binder component with a fine grain mineral fragment that has 90% of the fragments having a diameter of less than 150 microns. Such mineral granule is commercially available from The Andersons under the trade names DG-Lite and DH46.

A binder component is present in a mineral granule in an amount ranging from 0.1% to 70% by weight of the dry weight of the mineral granule. In a further embodiment, the binder component is present in an amount ranging from 1% to 25% by weight of the dry weight of the mineral granule. A binder component is included in a particle as necessary to produce or promote cohesion in forming a particle capable of retaining a specified form during transport and/or distribution. A binder component may be bentonite clay, carbohydrate, protein, lipid, synthetic polymer, glycolipid, glycoprotein, lipoprotein, lignin, a lignin derivative, a carbohydrate-based composition, and a combination thereof. In a preferred embodiment the binder component is a lignin derivative and is optionally calcium lignosulfonate. Alternatively, the binder component is selected from the group consisting of: a monosaccharide, a disaccharide, an oligosaccharide, a polysaccharide and combinations thereof. Specific carbohydrate binders illustratively include glucose, mannose, fructose, galactose, sucrose, lactose, maltose, xylose, arabinose, trehalose and mixtures thereof such as corn syrup; celluloses such as carboxymethylcellulose, ethylcellulose, hydroxyethylcellulose, hydroxy-methylethylcellulose, hydroxyethylpropylcellulose, methylhydroxyethyl-cellulose, methylcellulose; starches such as amylose, seagel, starch acetates, starch hydroxyethyl ethers, ionic starches, long-chain alkyl starches, dextrins, amine starches, phosphates starches, and dialdehyde starches; plant starches such as corn starch and potato starch; other carbohydrates such as pectin, amylopectin, xylan, glycogen, agar, alginic acid, phycocolloids, chitin, gum arabic, guar gum, gum karaya, gum tragacanth and locust bean gum; vegetable oils such as corn, soybean, peanut, canola, olive and cotton seed; complex organic substances such as lignin and nitrolignin; derivatives of lignin such as lignosulfonate salts illustratively including calcium lignosulfonate and sodium lignosulfonate and complex carbohydrate-based compositions containing organic and inorganic ingredients such as molasses. Suitable protein binders illustratively include soy extract, zein, protamine, collagen, and casein. Binders operative herein also include synthetic organic polymers capable of promoting or producing cohesion of particle components and such binders illustratively include ethylene oxide polymers, polyacrylamides, polyacrylates, polyvinyl pyrrolidone, polyethylene glycol, polyvinyl alcohol, polyvinylmethyl ether, polyvinyl acrylates, polylactic acid, and latex. In a preferred embodiment, the binder is calcium lignosulfonate, molasses, a liquid corn starch, a liquid corn syrup or a combination thereof. An aggregate dense mineral containing granule is produced by a number of processes. In the preferred process, the granule components are wet-granulated through a process of steps, including mixing of various dry components, wet-massing the dry powder mixture with liquid surfactants, binders or the like, alone or with the addition of a solvent to arrive at a suitable consistency for granulating. U.S. Pat. Nos. 6,231,660 and 6,613,138 are representative manufacturing process and composition for dense mineral containing granules conventional to the art.

A cellulosic granule component of an inventive vegetation culture active agent delivery medium has a bulk density of between 8 and 45 pounds per cubic foot. Typically, a cellulosic granule has a mean cellulosic granule size of from 297 microns to 3360 microns with fine cellulosic granules having a size of less than 297 microns constituting less than 5 weight percent of the cellulosic granules. More preferably, fine cellulosic granules constitute less than 2 percent of the cellulosic granule weight and most preferably less than 0.5 weight percent of the cellulosic granule material. Preferably, more than 95% of the cellulosic granules have a size between 40 microns and 3360 microns and most preferably between 595 microns and 2000 microns. While it is appreciated that the cellulosic granules operative herein are formed by aggregating smaller cellulosic fragments as detailed above with respect to the dense mineral containing granules, in a preferred embodiment the cellulosic granules are monolithic. Cellulosic materials operative herein illustratively include grain hulls, peanut hulls, corncob, wood dust, and dried distillers grain (DDG). The cellulosic granule component is readily formed through conventional techniques such as grinding and sieving, extrusion pelletization and sieving, and related techniques well known to the art. Cellulosic granules are typically present in a medium according to the present invention in an amount from 10 to 90 total weight percent of the medium.

The inventive combination of mineral granules of comparatively higher density and larger mean particle size relative to cellulosic granules with a lower density and smaller mean particle size provides for a larger dispersion volume relative to mineral-based granular materials as detailed in U.S. Pat. Nos. 6,231,660 or 6,613,138. The inclusion of cellulosic granule according to the present invention allows product total density to be adjusted to facilitate bag filling. Additional advantages achieved through the inventive combination include less mineral granule fragmentation during transport and as a result less product dusting during application. Still a further advantage includes a larger volume of material to be applied by the end user so as to favor lower active agent dispersion density per area of vegetation so as to reduce overall active agent usage, It is appreciated that conventional spreaders granulated products provide limited end user control over spreading density, adjustment of delivery medium according to the present invention is readily tailored to lessen over usage of active agents. A still further attribute of the inventive medium is water absorption by cellulosic material that in turn facilitates prolonged mineral granule wetting and dispersion into constituent mineral fragments.

Upon forming either of the mineral granules or the cellulosic granules, a formulation of an active agent is applied to the granules. It is appreciated that one can: apply one or more liquid active agents to the mineral granules and separately apply one or more liquid active agents to the cellulosic granules, or alternatively, mix the mineral granules and the cellulosic granules in a predetermined ratio and thereafter apply one or more active agents to the intermixed mineral granules and cellulosic granules. Preferably, the active agent is dissolved in a solvent and applied to the preformed mineral granules, cellulosic granules, or a combination thereof. Alternatively, it is appreciated that a liquid active agent formulation is incorporated into a binder solution during the formation of a mineral granule.

An active agent in powder form is intermixed with mineral granules and cellulosic granules to form the inventive delivery medium combination. The active agent granules are preferably of a mean size less than 20 percent that of the mean mineral granule size. Without intending to be bound to a particular theory, electrostatic forces are believed to be operative to retain active agent powder in contact with the granules of an inventive medium combination.

An active agent powder adhered to an inventive media granule includes any conventional active agent formulated as a powder. Preferably, active agent powder is sized such that the powder grain diameter has a mean particle diameter of less than 10% that of the mineral granules mean size. More preferably, the active agent powder has a mean diameter of less than 2% that of the mineral granules particle diameter. Effectively, any conventional active agent powder is operative within the present invention.

Active agents operative as part of an inventive combination illustratively include algicides, bacteriocides, defoliants, desiccants, fungicides, herbicides, insecticides, insect growth regulators, miticides, nematicides, ovicides, pesticides, pheromones, repellents, rodenticides; plant growth hormones and plant growth regulators; and pest reproductive control agents.

Pesticides suitable to form a liquid coating illustratively include pyrethroids such as bifenthrin, permethrin, deltamethrin, lambda cyhalothrin, cyfluthrin, or betacyfluthrin; organophosphates such as chlorpyrifos; limonoids such as azadirachtin or meliartenin; phenyl pyrazoles or oxadiazines such as indoxacarb; phthalic acid diamides such as flubendiamide and anthranilic diamides. Additionally, it is appreciated that a number of conventional adjuvant systems used to solubilize a pesticide for application as a coating onto a granule of inventive media are rendered more effective by the present invention. By way of example, pyrethroids degrade to yield organic acids that in proximity to certain pesticide powders such as carbamates function to extend the carbamate activity half-life.

Operative pesticide powders within the present invention illustratively include carbamates such as carbaryl (1-naphthyl N-methylcarbamate), neonicotinoids or nitroguanidines such imidacloprid, thiomethoxam, clothianidin or dinotefuran; diacylhydrazines such as halofenozide; neonicotines such as floconamid; organophosphates such as trichlorfon and pyrazoles such as fipronil. It is appreciated that multiple active pesticide agents are readily formulated within a pesticide powder operative herein.

Plant growth hormones and plant growth regulators illustratively includes cytokinins, auxins, gibberellins, ethylene, abscissic acid and a combination thereof.

For purpose of this invention, a pest reproductive control agent operative herein includes a pheromone, molting signaling compound or steroid that upon contact with the target pest decreases the reproductive capacity of the pest. A pest reproductive control agent is preferred over a pesticide since a reproductive control agent is specific to a species or narrower group of organisms, does not bioaccumulate, and is less detrimental to predatory or bystander organisms in the pest habitat. Additionally, a reproductive control agent is unlikely to avoid the bait due to ill health effects associated with sampling, as is often the case with a lethal pesticide.

The pest reproductive control agent includes agents such as an acaracide, an antimicrobial, a bactericide, an entomopathogen, a fungicide, a synthetic plant growth regulator such as a gibberlic acid synthesis inhibitor or promoter, an herbicide, an insecticide, a molluskicide, a nemacide, a rodenticide, a pheromone, a chemosterilant, a viricide, an imagocide, a larvicide, an ovicide, a formicide, an aphidicide, a muscacide, a culicicide, an anophelicide, an arachnidcide, and a vespacide. Preferably, an inventive bait particle containing a toxic invertebrate pesticide also contains a mammalian and/or avian ingestion repellant. More preferably, it also contains both mammalian and avian ingestion repellants to lessen the likelihood of incidental ingestion by bystander higher species. Mammalian ingestion repellants illustratively include cadaverine, butyric acid, and capsaicin. Avian repellants include artificial grape flavorant.

Herbicides, for purposes of this invention, include a wide array of chemical and biological compositions which include materials in the functional, or mode of action categories of desiccants, defoliants, abscission agents, algaecides, moss control agents (silvicides), acetyl coenzyme A carboxylase inhibitors, acetolactate synthase enzyme inhibitors, synthetic auxins (action like indoleacetic acid), inhibition of auxin transport, inhibitors of photosynthesis at photosystem II Site A and others with different binding behavior, inhibition of DHP (dihydropteroate) synthase, inhibition of acetyl CoAcarboxylase (ACCase), inhibition of lipid synthesis (not ACCase inhibition), inhibitors of 5-enolpyruvylshikimate-3-phosphate (EPSP) synthase or EPSPS inhibitor, inhibition of 4-hydroxyphenyl-pyruvate-dioxygenase (4-HPPD) (bleaching), inhibitors of glutamine synthetase, inhibitors of carotenoid biosynthesis, inhibition of carotenoid biosynthesis at the phytoene desaturase step (PDS) (bleaching), inhibition of all diterpenes, inhibitors of protoporphyrinogen oxidase (PPO), inhibitors of dihydropteroate (DHP) synthase step, inhibitors of indoleacetic acid action, inhibitors of cell wall (cellulose) synthesis, Site A inhibitors of cell wall synthesis, Site B photo system I-electron diverters, inhibition of photosynthesis at photosystem II, inhibitors of mitosis, uncoupling membrane disruptors, inhibition of 4-hydroxyphenyl-pyruvatedioxygenase (4-HPPD), enolpyruvylshikimate 3-phosphate synthase enzyme inhibitors, synthetic auxins, uncoupling (membrane disruption), inhibition of VLCFAs (inhibition of cell division), inhibition of mitosis/microtubule organization, microtubule assembly inhibition, and other, unknown mechanisms. Biological, or biorational, herbicides with application to this invention fall generally into the categories of bacteria, fungi, viruses, and plants, including the spore and other reproductive forms thereof, extracts derived therefrom, and including naturally occurring and genetically engineered forms.

More particularly, herbicides commonly fall into one (or more, in the case of mixtures) of the following chemical families: aryloxyphenoxy propionates, arylarninopropionic acid, arsenicals, cineole (such as cinmethylin), cyclohexanediones, sulfonylureas, imidazolinones, pyrimidinylthiobenzoate, triazolopyrimidine, dinitroanilines, pyridazine, phenoxys (or phenoxies), benzoic acids, carboxylic acids (such as DCPA, clopyralid, trichloroacetic acid, and flouroxypyr), quinoline carboxylic acid, semicarbazone, triazines, triazinones, uracils, pyridazinone, phenyl-carbamates, nitrites, benzothiadiazoles, organoarsenicals, phenylpyridazine, ureas and substituted ureas (such as diuron, linuron, siduron, tebuthiuron, dymron etc.), amide (such as propanil and bromobutide), thiocarbamates, organophosphates (such as bensulide), pyrazolium (such as difenzoquat), phosphoric acid compounds (such as glufosinate-ammonium and glyphosate), triazole, pyridazinone, nicotinanilide, pyridinone (such as fluridone), isoxazolidinone, diphenylethers, N-phenylphthalimides, oxadiazole, triazolinone, chloroacetamides, oxyacetamides, carbamate (such as asulam), phthalamate, phthalamate semicarbazone, nitrile, N-phenylphthalimides, oxadiazole, triazolinone, acetamides, benzoylisoxazole, isoxazole, pyrazole, pyrazolium, trilcetone, and benzofuran, biological herbicides including *Pitcciiia canaliculata, Puccinai jacea, Xanthomonas campestris, Alternaria destruens, Colletotrichum gloeosposioides, Dendryphion papaveraceae, Pseudomonas syrinzgae,* including any varieties or subspecies thereof. Examples of plant extract herbicides are corn gluten meal and the allelopathic exudates of various plants.

It is appreciated that multiple grades or compositions of dense material containing granules are used in place of a single type of dense mineral containing granules with multiple grades varying in a property of density, granule composition, active agent component, mean particle size, or a combination thereof. Likewise, multiple cellulosic granule grades are readily substitutable for single distribution of cellulosic granules.

The present invention is further detailed with respect to the following nonlimiting examples which embody particular aspects of the present invention, but should not be construed as a limitation on the invention as recited in the appended claims.

EXAMPLE 1

A limestone based dense mineral granule formulation is prepared according to Examples 1-7 of U.S. Pat. No. 6,231,660 to yield a 1.5 millimeters mean size dense mineral containing granules having a density of 62 pounds per cubic foot and an index of uniformity of between 20 and 60. Forty parts by weight of the resultant dense mineral containing granules are mixed with 60 parts per weight of peanut hull ground to a mean size guide of 2 millimeters and an index of uniformity of between 20 and 60 to yield a mixture density of 35.75 pounds per cubic foot. The resultant material is mixed with 0.1 parts by weight of λ-cyhalothrin. The resulting material is packaged in 50 pound bags and transported to an end use field where the material was spread with a rotary spreader. As a comparative, 1 part of λ-cyhalothrin was combined with 100 parts by weight of only dense material containing granules and as a separate comparative with 100 parts by weight of only cellulosic granules. The end user noted greater ease of spreading for the inventive combination material as relative to the comparatives with an active distribution per unit area of ground more closely aligned to target area loadings relative to the comparatives. It was also noted that a large portion of the granules disperse when contacted with rain or irrigation which has many benefits like increased efficacy and less risk of non-target pickup.

EXAMPLE 2

The delivery medium of Example 1 was reproduced with the replacement of the peanut hull with extruded pelletized corncob of the same mean size and distribution. Fifty parts by weight of the dense material containing granules of Example 1 are mixed with 50 parts by weight of extruded pelletized corncob to yield a material having a density of 37.5 pounds per cubic foot. The results for this delivery medium were comparable to those for the inventive medium of Example 1.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A vegetation culture active agent delivery medium having an overall density and comprising:

a plurality of mineral granules containing at least 30 percent by weight of a mineral, said mineral having a bulk density of greater than 70 pounds per cubic foot and a mean mineral granule size, each of said plurality of mineral granules comprises a plurality of mineral fragments and a binder joining said plurality of mineral fragments;

a plurality of cellulosic granules having a bulk density of between 8 and 45 pounds per cubic foot and a mean cellulosic granule size; and a vegetation culture active agent in simultaneous contact with said plurality of mineral granules and said plurality of cellulosic granules, said active agent being present from $1\times10^{-5}$ to 10 total weight percent of the medium, wherein water absorption by said plurality of cellulosic granules facilitates prolonged wetting and dispersion of said plurality of mineral granules into said plurality of mineral fragments and the mean mineral granule size is larger than the mean cellulosic granule size.

2. The medium of claim 1 wherein the mean mineral granule size is from 500 to 3000 microns.

3. The medium of claim 2 wherein more than 90 number percent of said plurality of mineral fragments have a size less than 150 microns.

4. The medium of claim 1 wherein said plurality of mineral fragments are each independently selected from the group consisting of: dolomite, limestone, gypsum, and pelletized lime.

5. The medium of claim 1 wherein said binder is selected from the group consisting of: lignin, bentonite clay, carbohydrate, protein, lipid, synthetic polymer, glycolipid, glycoprotein, and lipoprotein.

6. The medium of claim 1 wherein said mean cellulosic granule size is between 297 and 3360 microns.

7. The medium of claim 1 wherein said plurality of cellulosic granules are each a monolithic cellulosic fragment.

8. The medium of claim 7 wherein said monolithic cellulosic fragment is composed of a material selected from the group consisting of grain hull, peanut hull, corncob, wood dust, and dried distiller grain.

9. The medium of claim 1 wherein said active agent is selected from the group consisting of algicide, bacteriocide, defoliant, desiccant, fungicide, herbicide, insecticide, insect growth regulator, miticide, nematicide, ovicide, pheromone, repellent, rodenticide, plant growth hormone, and plant growth regulator.

10. The medium of claim 1 wherein said active agent is a pesticide.

11. The medium of claim 1 wherein said active agent is a powder having a mean particle size less than 20 percent of the mean mineral granule size.

12. The medium of claim 1 wherein said active agent is a powder having a mean particle size less than 2 percent of the mean mineral granule size.

13. The medium of claim 1 wherein said active agent is a liquid coating.

14. The medium of claim 1 having an overall density of between 35 and 60 pounds per cubic foot.

15. A vegetation culture active agent delivery medium having an overall density and consisting essentially of between 35 and 60 pounds per cubic foot:

a plurality of mineral granules containing at least 30 percent by weight of a mineral, said mineral having a bulk density of greater than 70 pounds per cubic foot and a mean mineral granule size, each of said plurality of mineral granules comprises a plurality of mineral fragments and a binder joining said plurality of mineral fragments;

a plurality of cellulosic granules having a bulk density of between 8 and 45 pounds per cubic foot and a mean cellulosic granule size; and a vegetation culture active agent in simultaneous contact with said plurality of mineral granules and said plurality of cellulosic granules, said active agent being present from $1\times10^{-5}$ to 10 total weight percent of the medium, wherein water absorption by said plurality of cellulosic granules facilitates prolonged wetting and dispersion of said plurality of mineral granules into said plurality of mineral fragments and the mean mineral granule size is larger than the mean cellulosic granule size.

16. The medium of claim 15 wherein the mean mineral granule size is from 500 to 3000 microns.

17. The medium of claim 16 wherein more than 90 number percent of said plurality of mineral fragments have a size less than 150 microns.

18. The medium of claim 15 wherein said plurality of cellulosic granules are each a monolithic cellulosic fragment.

19. The medium of claim 16 wherein said active agent is a pesticide.

* * * * *